(12) United States Patent
Eguchi et al.

(10) Patent No.: US 7,337,073 B2
(45) Date of Patent: Feb. 26, 2008

(54) ACTIVITY EVALUATION METHOD FOR EVALUATION OF TARGET COMPOUNDS USING FUKUI FUNCTION

(75) Inventors: Haruki Eguchi, Yokohami (JP); Yoshihiro Ishikawa, 1-19-8, Shinjuku, Shinjuku, Tokyo (JP); Kousaki Iwatsubo, Yokohama (JP)

(73) Assignees: Ishikawajima-Harima Heavy Industries Co., Ltd. (JP); Yoshihiro Ishikawa (JP)

( * ) Notice: Subject to any disclaimer, the term of this patent is extended or adjusted under 35 U.S.C. 154(b) by 0 days.

(21) Appl. No.: 11/442,478

(22) Filed: May 26, 2006

(65) Prior Publication Data

US 2007/0050148 A1    Mar. 1, 2007

(30) Foreign Application Priority Data

Aug. 31, 2005    (JP) .......................... P2005-251189

(51) Int. Cl.
*G06F 19/00*    (2006.01)
*G06G 7/60*    (2006.01)

(52) U.S. Cl. .......................................... 702/19; 703/11
(58) Field of Classification Search ..................... None
See application file for complete search history.

(56) References Cited

OTHER PUBLICATIONS

Beck. M. E., J. Chem. Inf. Model., vol. 45, pp. 273-282, Mar.-Apr. 2005.*
Type-Specific Regulation of Adenylyl Cyclase—The Journal of Biological Chemistry—2001 by the American Society for Biochemistry and Molecular Biology, Inc.—vol. 276, No. 51, Issue of Dec. 21-pp. 47785-47793, 2001.

* cited by examiner

*Primary Examiner*—John S Brusca
(74) *Attorney, Agent, or Firm*—Ostrolenk, Faber, Gerb & Soffen, LLP

(57) ABSTRACT

In an activity evaluation method for an evaluation target compound, among atoms constituting the evaluation target compound, one or more are set as analysis points, and an activity of the evaluation target compound with respect to a high molecular compound is calculated based on a predetermined evaluation expression having Fukui function values as variables obtained by numerical calculation for the set analysis points.

5 Claims, 6 Drawing Sheets

| Compound | Position | | |
|---|---|---|---|
| | $R_6$ | $R_7$ | $R_{13}$ |
| Forskolin | H | $CH_3$ | $CH=CH_2$ |
| FD1 | $CONHCH_2CH_2NCS$ | $CH_3$ | $CH=CH_2$ |
| FD2 | $COCH_2CH_2CH_2COCH=CH_2$ | $CH_3$ | $CH=CH_2$ |
| FD3 | H | NHOH | $CH=CH_2$ |
| FD4 | 5,6-dihydroxy | (pyridine ring) | $CH=CH_2$ |
| FD5 (NKH477) | $COCH_2CH_2N(CH_3)_2$ | $CH_3$ | $CH=CH_2$ |
| FD6 | $COCH_2CH_2N(CH_3)_2$ | $CH_3$ | $CH_2CH_3$ |

FIG.4

| LUMO $f_K^+$ | C1 | C2 | C3 | C4 | C5 | C6 | C7 | C8 | C9 | C10 | C11 | C12 | C13 |
|---|---|---|---|---|---|---|---|---|---|---|---|---|---|
| Forskolin | -0.018 | -0.012 | -0.012 | -0.011 | -0.010 | -0.005 | -0.004 | -0.014 | 0.009 | 0.000 | 0.184 | -0.058 | -0.020 |
| FD1 | -0.014 | -0.010 | -0.010 | -0.008 | -0.008 | -0.002 | -0.002 | -0.011 | 0.006 | 0.000 | 0.145 | -0.043 | -0.014 |
| FD2 | -0.001 | -0.004 | -0.008 | -0.001 | -0.008 | -0.007 | -0.004 | 0.004 | 0.000 | 0.000 | -0.002 | -0.002 | -0.006 |
| FD3 | -0.017 | -0.012 | -0.011 | -0.010 | -0.010 | -0.004 | -0.003 | -0.018 | 0.007 | 0.000 | 0.173 | -0.048 | 0.000 |
| FD4 | -0.009 | -0.011 | -0.013 | -0.022 | 0.001 | 0.073 | 0.011 | 0.012 | -0.005 | 0.001 | 0.001 | -0.007 | -0.008 |
| FD5 | -0.017 | -0.009 | -0.012 | -0.008 | -0.008 | 0.000 | 0.001 | -0.018 | -0.009 | -0.002 | 0.196 | -0.046 | -0.012 |
| FD6 | -0.015 | -0.011 | -0.015 | -0.009 | -0.010 | 0.000 | -0.002 | -0.017 | 0.003 | 0.000 | 0.188 | -0.054 | -0.015 |

FIG.5

| HOMO $f_K^-$ | C1 | C2 | C3 | C4 | C5 | C6 | C7 | C8 | C9 | C10 | C11 | C12 | C13 |
|---|---|---|---|---|---|---|---|---|---|---|---|---|---|
| Forskolin | -0.041 | -0.023 | -0.022 | -0.012 | -0.010 | -0.005 | 0.001 | -0.001 | -0.001 | -0.010 | 0.017 | -0.009 | -0.017 |
| FD1 | -0.014 | -0.022 | -0.021 | -0.010 | -0.009 | 0.002 | 0.001 | -0.001 | -0.002 | -0.009 | 0.016 | -0.006 | -0.017 |
| FD2 | -0.010 | -0.008 | -0.010 | -0.003 | -0.008 | -0.005 | -0.003 | 0.003 | 0.000 | -0.002 | 0.000 | -0.002 | -0.007 |
| FD3 | -0.039 | -0.022 | -0.021 | -0.011 | -0.010 | -0.005 | 0.000 | -0.002 | -0.002 | -0.009 | 0.016 | -0.003 | -0.006 |
| FD4 | -0.009 | -0.011 | -0.013 | -0.021 | 0.001 | 0.077 | 0.012 | 0.012 | -0.005 | 0.002 | 0.001 | -0.007 | -0.008 |
| FD5 | -0.006 | -0.006 | -0.010 | -0.005 | -0.006 | -0.002 | -0.002 | -0.003 | -0.003 | -0.004 | 0.011 | -0.005 | -0.013 |
| FD6 | -0.005 | -0.007 | -0.012 | -0.005 | -0.008 | -0.007 | -0.003 | -0.002 | -0.002 | -0.003 | 0.012 | -0.005 | -0.013 |

ACTIVITY EVALUATION METHOD FOR EVALUATION OF TARGET COMPOUNDS USING FUKUI FUNCTION

BACKGROUND OF THE INVENTION

1. Field of the Invention

The present invention relates to an activity evaluation method for an evaluation target compound.

Priority is claimed on Japanese Patent Application No. 2005-251189, filed Aug. 31, 2005, the content of which is incorporated herein by reference.

2. Description of Related Art

In the development of a drug, the activity of a drug candidate agent with respect to a protein serving as one of the high molecular compounds constituting a living body, is evaluated. That is, a drug having a low activity with respect to a protein is not appropriate as a drug candidate agent, and such drugs having a low activity are excluded from the drug candidate agent. However, several hundred thousand types of proteins or more are present, and there are proteins having similar functions but having different organ expressions/biochemical properties (protein subtype). For example, in a prior art document (Non Patent Document 1: Takeshi Onda et al., J. Bio. Chem., 276 (2001) 47785-47793), there is disclosed experimental results for where various types of forskolin derivatives being forskolins having side chains modified, were produced as drug candidate agents, and the activities of these forskolin derivatives with respect to adenylate cyclase (type II, type III, and type V subtypes) serving as a protein were experimentally obtained.

Incidentally, in the development of a drug, the long development term has been a big problem. By shortening the development term, superiority with respect to competitors can be ensured, and development costs can be significantly reduced. However, as mentioned above, in order to evaluate the activity of a forskolin derivative with respect to a protein, for example adenylate cyclase, and to evaluate for each subtype of a plurality of existing adenylate cyclase, there is no other way than to obtain the activity by experiment. This experiment requires a huge amount of time and labor, and special techniques. Therefore there has been a problem of extremely poor efficiency in the conventional activity evaluation method.

SUMMARY OF THE INVENTION

The present invention addresses the abovementioned problems, with an object of evaluating the activity of an evaluation target compound with respect to a high molecular compound within a shorter time than heretofore.

In order to achieve the above object, as a first solution, the present invention employs a means for: setting as analysis points one or more atoms among atoms constituting an evaluation target compound; and calculating an activity of the evaluation target compound with respect to a high molecular compound, based on a predetermined evaluation expression having Fukui function values as variables obtained by numerical calculation for the analysis points.

Moreover, in the present invention, as a second solution, in the first solution: a first Fukui function value $f_k^+$ showing a nucleophilic reaction, and a second Fukui function value $f_k^-$ showing an electrophilic reaction are obtained for each of the analysis points k by means of numerical calculation; and an activity P of the evaluation target compound with respect to the high molecular compound is calculated, based on the following evaluation expression (5) composed of a first coefficient $D_k^+$ related to the first Fukui function value $f_k^+$, and a second coefficient $D_k^-$ related to the second Fukui function value $f_k^-$:

$$P = \sum_{k=1}^{n} (D_k^+ \cdot f_k^+ + D_k^- \cdot f_k^-) \tag{5}$$

(where n is the total number of analysis points k)

Moreover, in the present invention, as a third solution, in the second solution, the least-squares method is applied to an activity experimental value $P_e$ related to a plurality of derivatives of the evaluation target compound, and a first Fukui function value $f_k^+$ and a second Fukui function value $f_k^-$ related to the respective derivatives, to thereby calculate a first coefficient $D_k^+$ showing a relation between the activity P and the first Fukui function value $f_k^+$, and a second coefficient $D_k^-$ showing a relation between the activity P and the second Fukui function value $f_k^-$.

Moreover, in the present invention, as a fourth solution, in the second solution, a plurality of equations obtained by substituting an activity experimental value $P_e$ related to a plurality of derivatives of the evaluation target compound, and a first Fukui function value $f_k^+$ and a second Fukui function value $f_k^-$ related to the respective derivatives, into the evaluation expression, are solved as simultaneous equations, to thereby calculate the first coefficient $D_k^+$ and the second coefficient $D_k^-$.

Furthermore, in the present invention, as a fifth solution, in the third and fourth solutions, among the atoms constituting the respective derivatives of the evaluation target compound, an atom which is commonly present in the respective derivatives is set as an analysis point.

Moreover, in the present invention, as a sixth solution, in the first solution, the high molecular compound is a protein.

Furthermore, in the present invention, as a seventh solution, in the first solution, the evaluation target compound is a drug candidate agent.

According to the present invention, among the atoms constituting the evaluation target compound, one or more are set as analysis points, and the activity of the evaluation target compound with respect to the high molecular compound is calculated based on a predetermined evaluation expression having Fukui function values as variables obtained by numerical calculation for the set analysis points. Therefore, the activity can be calculated by merely substituting the Fukui function value that has been obtained by the numerical calculation, into the evaluation expression, thus enabling evaluation of the activity in a very short time compared to the conventional activity evaluation method based on experiment.

BRIEF DESCRIPTION OF THE DRAWINGS

FIG. 4 shows calculated values of LUMO$f_k^+$ in respective analysis points of various forskolin derivatives in one embodiment of the present invention.

FIG. 5 shows calculated values of $HOMOf_k^-$ in respective analysis points of various forskolin derivatives in one embodiment of the present invention.

DETAILED DESCRIPTION OF THE INVENTION

Hereunder is a description of one embodiment of the present invention, with reference to the drawings.

The present embodiment relates to an activity evaluation method for a drug candidate agent serving as an evaluation target compound, more specifically a forskolin derivative, with respect to a protein as a high molecular compound, more specifically adenylate cyclase.

Figure 1:
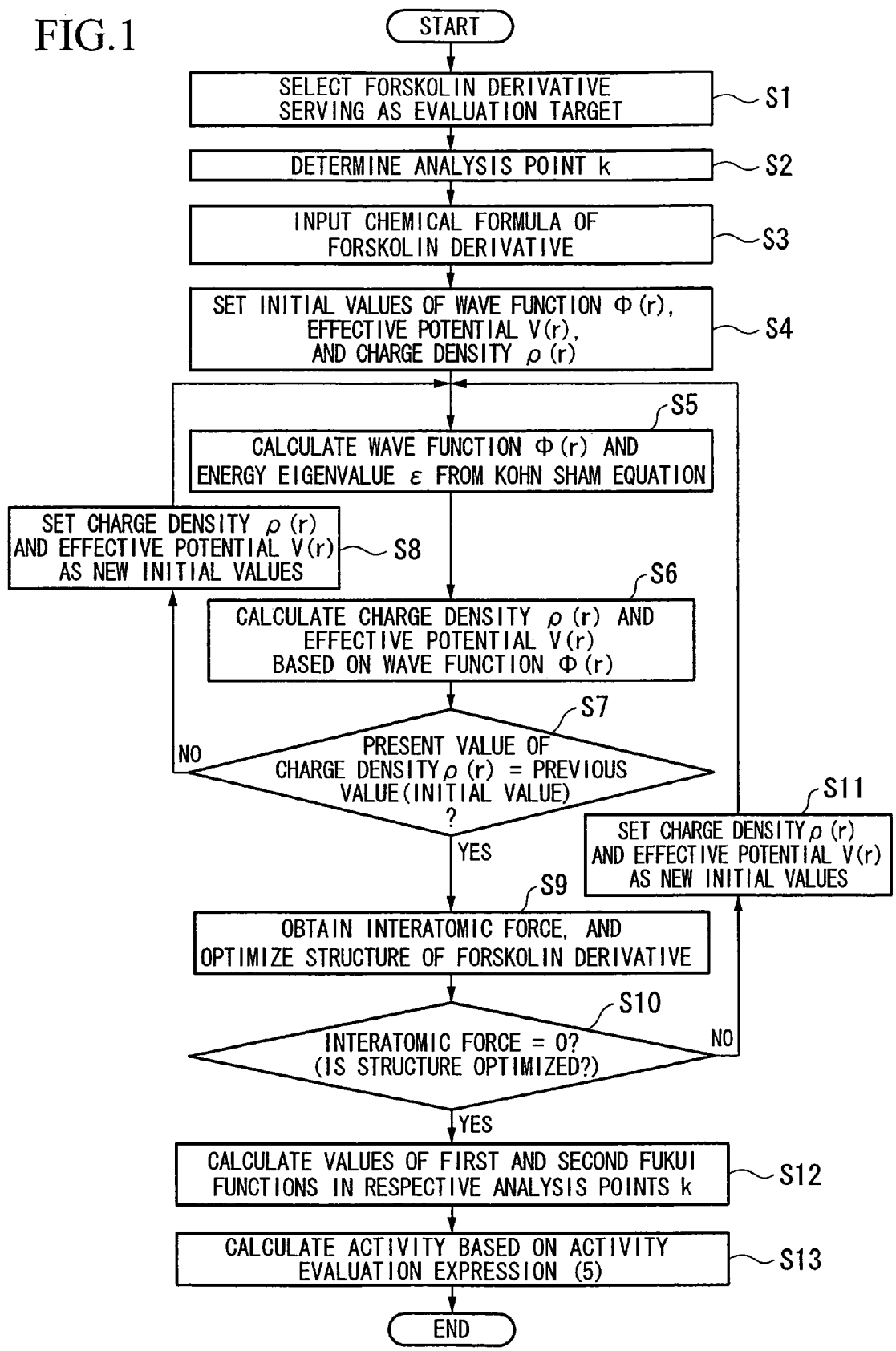
FIG. 1 is a flow chart showing a processing procedure of an activity evaluation method according to one embodiment of the present invention.
Figures 2, 3:
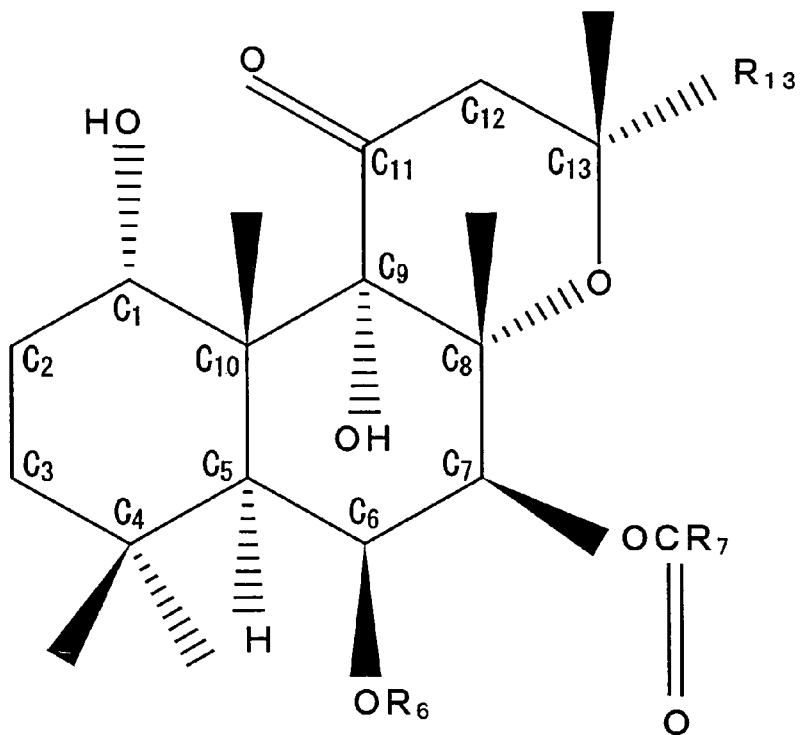
FIG. 2 is a diagram of a molecular structural model of a forskolin derivative in one embodiment of the present invention.
FIG. 3 shows types of side chains bonded to forskolin derivatives in one embodiment of the present invention.

FIG. 1 is a flow chart showing a processing procedure of the present activity evaluation method. Firstly, a forskolin derivative to be an evaluation target is selected (step S1). FIG. 2 is a schematic diagram showing a molecular structure of a forskolin derivative. In this drawing, $R_6$, $R_7$, and $R_{13}$ show positions bonded with an atom or a molecule for modifying a side chain of the forskolin derivative. Depending on the types of atom or molecule bonded to these positions, the physical property of the forskolin derivative varies. Specifically, the activity with respect to adenylate cyclase varies. FIG. 3 shows examples of atoms and molecules for modifying side chains of a forskolin derivative. In FIG. 3, "Forskolin" having H bonded to $R_6$, $CH_3$ bonded to $R_7$, and $CH=CH_2$ bonded to $R_{13}$ is the only forskolin present in the natural world, and the other "FD1" to "FD6" are forskolins which are artificially produced by changing the side chain structure. Such forskolin having the artificially changed side chain structure is called a forskolin derivative. In the present embodiment, the forskolin derivative "FD5" shown in FIG. 3 is selected as an evaluation target, and described hereunder. The following steps S2 to S13 are steps for obtaining the activity of the forskolin derivative that has been selected as the evaluation target, with respect to adenylate cyclase, by a computer simulation based on the first principle calculation method. The processing described hereunder is performed in a computer simulation.

Now, as described above, after the forskolin derivative "FD5" serving as the evaluation target is selected, the chemical formula of the forskolin derivative "FD5" is input into a computer simulation (step S2). Then, among the C (carbon) in the benzene rings constituting the forskolin derivative "FD5", any one or more are determined (input) as an analysis point (step S3). In the present embodiment, as shown in FIG. 2, $C_1$ to $C_{13}$ are determined as analysis points. Hereunder, C corresponding to the analysis point k (k=1 to 13) is described as $C_k$.

As described above, similarly to the $C_k$ in the benzene rings, an atom which is commonly present in respective derivatives, that is, an atom which is present in a stable position, is determined as an analysis point, thereby enabling the activity described below to be accurately obtained. Moreover, as the number of the analysis points k becomes greater, the activity can be more accurately obtained.

Subsequently, based on the chemical formula of the forskolin derivative "FD5", initial values of the wave function $\Phi(r)$, the effective potential $V(r)$, and the charge density $\rho(r)$ are set and input (step S4). In these wave function $\Phi(r)$, effective potential $V(r)$, and charge density $\rho(r)$, r is a variable showing the coordinates in three dimensional space.

In the case where the respective atoms constituting the forskolin derivative "FD5" are present as an isolated atom in three dimensional space, the wave functions $\Phi(r)$ are obtained for each of the respective atoms. The initial value of the wave function $\Phi(r)$ is the sum of all the wave functions that have been obtained for each of the respective atoms. Similarly, the initial value of the effective potential $V(r)$ is the sum of all the effective potentials obtained for each of the respective atoms based on the wave functions in the case where the respective atoms constituting the forskolin derivative "FD5" are present as an isolated atom in three dimensional space. Moreover, the initial value of the charge density $\rho(r)$ is obtained by substituting the initial value of the wave function $\Phi(r)$ into the following operational expression (1). In the following operational expression (1), $\Phi^*(r)$ is a conjugate complex number of the wave function $\Phi(r)$.

$$\rho(r) = \Sigma \Phi^*(r)\Phi(r) \tag{1}$$

Next, based on the initial value of the effective potential $V(r)$ and the initial value of the charge density $\rho(r)$, the following Kohn Sham equation (2) is solved to thereby calculate the wave function $\Phi(r)$ and the energy eigenvalue $\epsilon$ of the forskolin derivative "FD5" (step S5).

$$\left[-\frac{1}{2}\nabla^2 + V\{r, \rho(r)\}\right]\Phi(r) = \epsilon\Phi(r) \tag{2}$$

Then, based on the wave function $\Phi(r)$ of the forskolin derivative "FD5" obtained in step S4, the charge density $\rho(r)$ and the effective potential $V(r)$ of the forskolin derivative "FD5" are calculated (step S6), and it is judged whether or not this charge density $\rho(r)$ is the same as the previous value of the charge density $\rho(r)$, that is, the initial value here (step S7). In this step S7, if it is judged "NO", that is, the previous value (initial value) of the charge density $\rho(r)$ is not the same as the present value of the charge density $\rho(r)$ obtained in step S6, then the effective potential $V(r)$ and the charge density $\rho(r)$ obtained in step S6 are set as new initial values (step S8). The flow then proceeds to step S5, and the Kohn Sham equation (2) is solved again, so as to calculate a new wave function $\Phi(r)$ and energy eigenvalue $\epsilon$. That is, in step S7, by repeating the processing of steps S5 to S8 until the previous value of the charge density $\rho(r)$ becomes equal to the present value, the wave function $\Phi(r)$ and the energy eigenvalue $\epsilon$ satisfying the Kohn Sham equation (2) are obtained.

On the other hand, in step S7, if it is judged "YES", that is, the previous value of the charge density $\rho(r)$ is the same as the present value, then the wave function $\Phi(r)$ and the energy eigenvalue $\epsilon$ satisfying the Kohn Sham equation (2) are obtained. Therefore, based on these wave function $\Phi(r)$ and energy eigenvalue $\epsilon$, an interatomic force acting between respective atoms is calculated, and the structure of the forskolin derivative "FD5" is optimized (step S9). That is, the wave function $\Phi(r)$ and so forth that have been obtained by repeating steps S5 to S8, are merely the optimum values in a model on a two dimensional plane as shown in FIG. 2, and in practice it is necessary to consider the structure of the forskolin derivative "FD5" in the three dimensional space.

Specifically, in step S9, the respective atoms constituting the forskolin derivative "FD5" are moved for a predetermined distance in an optimum direction assumed from the wave function Φ(r), in the three dimensional space, and the interatomic force acting between the respective atoms at this time is calculated. When the interatomic force at this time becomes 0 and the respective atoms are not moved, it can be judged that the structure of the forskolin derivative "FD5" is optimized. Therefore, the interatomic force acting between the respective atoms after the movement is calculated, and it is judged whether or not the interatomic force becomes 0 (step S10). In this step S10, if it is judged "NO", that is, the interatomic force is not 0 and the structure is not optimized, then the wave function Φ(r) in the structure of the respective atoms after the movement is obtained, the effective potential V(r) and the charge density ρ(r) obtained from the wave function Φ(r) are set as new initial values (step S11), and the processing of steps S5 to S9 is repeated. Here, the reason why the flow returns to step S5 is that the wave function Φ(r) is changed due to the structural change of the respective atoms after the movement.

On the other hand, in this step S10, if it is judged "YES", that is, the interatomic force acting between the respective atoms becomes 0 and the structure of the forskolin derivative "FD5" is optimized, then the charge density ρ(r) in each analysis point $C_k$ is obtained, based on the wave function Φ(r) in the optimized structure. By substituting this charge density ρ(r) into the following first Fukui function (3) showing the nucleophilic reaction and second Fukui function (4) showing the electrophilic reaction, $LUMOf_k^+$ as the first Fukui function value (3) and $HOMOf_k^-$ as the second Fukui function value (4) in each analysis point $C_k$ are calculated (step S12).

LUMO: lowest unoccupied molecular orbital (Nucleophilic)

$$f^+(r) = \frac{1}{\Delta N}\{\rho_{N+\Delta}(r) - \rho(r)\} \quad (3)$$

HOMO: highest occupied molecular orbital (Electrophilic)

$$f^-(r) = \frac{1}{\Delta N}\{\rho_N(r) - \rho_{N-\Delta}(r)\} \quad (4)$$

Then, as described above, after $LUMOf_k^+$ and $HOMOf_k^-$ in each analysis point $C_k$ are obtained, they are substituted into the following activity evaluation expression (5) to thereby calculate the activity P of the forskolin derivative "FD5" with respect to adenylate cyclase (step S13). Since there are subtypes in adenylate cyclase, in practice, the activity $P_i$ is calculated based on the activity evaluation expression (6) unique to this subtype i.

$$P = \sum_{k=1}^{n}(D_k^+ \cdot f_k^+ + D_k^- \cdot f_k^-) \quad (5)$$

$$P_i = \sum_{k=1}^{n}(D_{i,k}^+ \cdot f_k^+ + D_{i,k}^- \cdot f_k^-) \quad (6)$$

In the activity evaluation expression (6), $D_{i,k}^+$ denotes a first coefficient related to $LUMOf_k^+$, $D_{i,k}^-$ denotes a second coefficient related to $HOMOf_k^-$, n denotes the total number of the analysis points k, and i denotes a subtype of adenylate cyclase. For example, in a case of i=V, $P_V$ denotes the activity with respect to the type V adenylate cyclase, $D_{V,k}^+$ denotes the first coefficient, and $D_{V,k}^-$ denotes the second coefficient thereof. In a case of i=II, $P_{II}$ denotes the activity with respect to the type II adenylate cyclase, and so forth. That is, since the first coefficient $D_{i,k}^+$ and the second coefficient $D_{i,k}^-$ vary according to the subtype i of adenylate cyclase, an activity evaluation expression (6) unique to the subtype i of adenylate cyclase exists.

Figure 6:
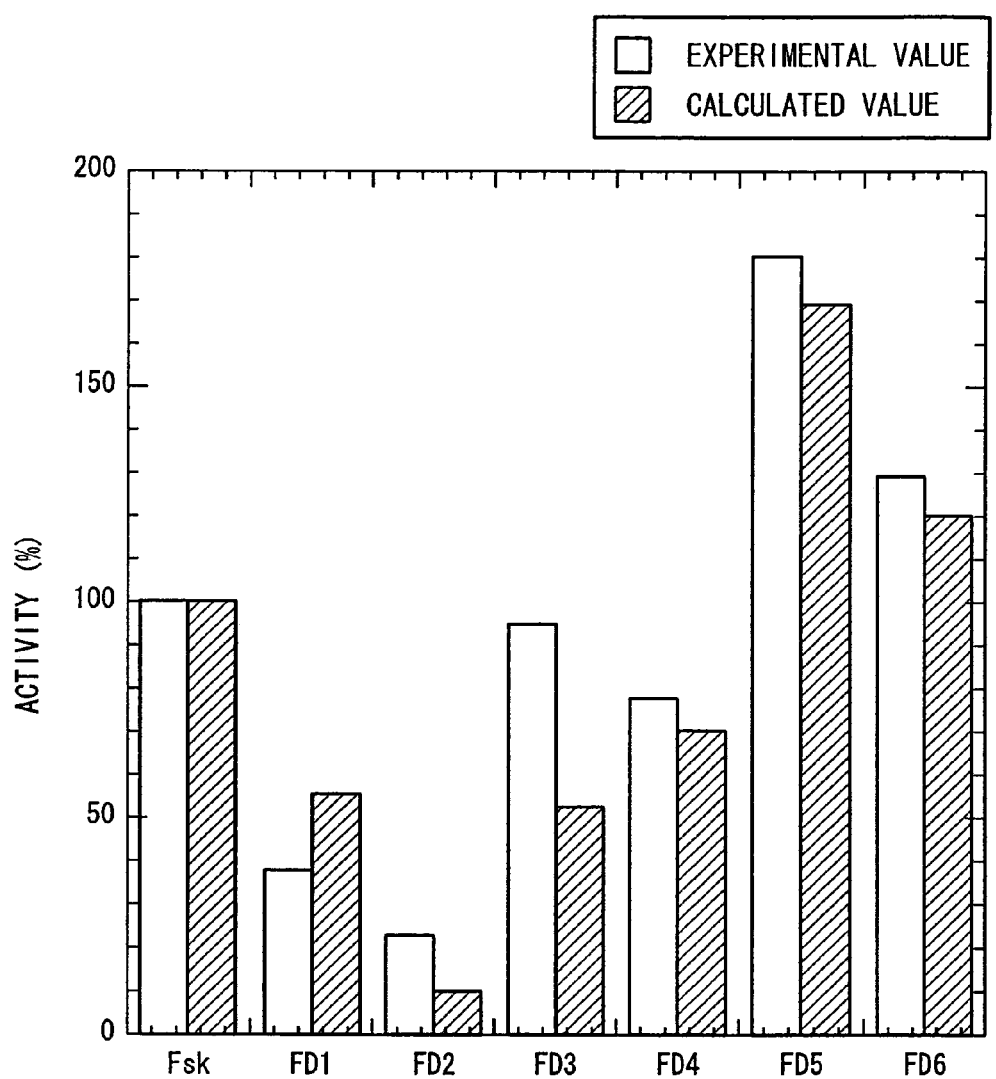
FIG. 6 is a bar chart showing experimental values and calculated values related to activities of various forskolin derivatives with respect to type V adenylate cyclase in one embodiment of the present invention.

Here is a description of a method of setting the first coefficient $D_{i,k}^+$ and the second coefficient $D_{i,k}^-$. FIG. 4 shows calculated values of $LUMOf_k^+$ related to analysis points $C_1$ to $C_{13}$ in the forskolin and the forskolin derivatives "FD1" to "FD6", by means of numerical calculation. Moreover, similarly, FIG. 5 shows calculated values of $HOMOf_k^-$ related to the analysis points $C_1$ to $C_{13}$ in the forskolin and the forskolin derivatives "FD1" to "FD6", by means of numerical calculation. FIG. 6 shows experimental values (white bar chart in FIG. 6) showing activities of the forskolin and the forskolin derivatives "FD1" to "FD6", with respect to subtype i=V, that is, type V adenylate cyclase. In FIG. 6, the vertical axis shows the activity assuming that the activity of the forskolin present in the natural world is 100%.

For example, focusing on to the forskolin derivative "FD5", $LUMOf_k^+$ and $HOMOf_k^-$ related to the forskolin derivative "FD5" are extracted from FIG. 4 and FIG. 5, and the experimental value of the activity related to the forskolin derivative "FD5" is extracted from FIG. 6. By substituting them into the activity evaluation expression (6), the following equation (7) is obtained.

$$\begin{aligned}
1.8 = & \{D_{v,1}^+ \cdot (-0.017)\} + \{D_{v,1}^- \cdot (-0.006)\} + \\
& \{D_{v,2}^+ \cdot (-0.009)\} + \{D_{v,2}^- \cdot (-0.006)\} + \{D_{v,3}^+ \cdot (-0.012)\} + \\
& \{D_{v,3}^- \cdot (-0.01)\} + \{D_{v,4}^+ \cdot (-0.008)\} + \{D_{v,4}^- \cdot (-0.005)\} + \\
& \{D_{v,5}^+ \cdot (-0.008)\} + \{D_{v,5}^- \cdot (-0.006)\} + \{D_{v,6}^+ \cdot (0)\} + \\
& \{D_{v,6}^- \cdot (-0.002)\} + \{D_{v,7}^+ \cdot (0.001)\} + \{D_{v,7}^- \cdot (-0.002)\} + \\
& \{D_{v,8}^+ \cdot (-0.018)\} + \{D_{v,8}^- \cdot (-0.003)\} + \{D_{v,9}^+ \cdot (-0.009)\} + \\
& \{D_{v,9}^- \cdot (-0.003)\} + \{D_{v,10}^+ \cdot (-0.002)\} + \{D_{v,10}^- \cdot (-0.004)\} + \\
& \{D_{v,11}^+ \cdot (0.196)\} + \{D_{v,11}^- \cdot (0.011)\} + \{D_{v,12}^+ \cdot (-0.046)\} + \\
& \{D_{v,12}^- \cdot (-0.005)\} + \{D_{v,13}^+ \cdot (0.012)\} + \{D_{v,13}^- \cdot (-0.013)\}
\end{aligned} \quad (7)$$

As is understood from the above equation (7), first coefficients $D_{V,k}^+$ and second coefficients $D_{V,k}^-$ which are 26 unknown numbers in total, are given. That is, equation (7) is obtained for 26 types of forskolin derivatives, and by solving the simultaneous linear equations consisting of these 26 equations, it is possible to obtain the first coefficient $D_{V,k}^+$ and the second coefficient $D_{V,k}^-$ with respect to the type V adenylate cyclase. Alternatively, by applying the multi variable least-squares method to the values of $LUMOf_k^+$ and $HOMOf_k^-$ shown in FIG. 4 and FIG. 5, and the experimental value of activity shown in FIG. 6, it is also possible to obtain the first coefficient $D_{V,k}^+$ and the second coefficient $D_{V,k}^-$. Experiments related to the activity of various forskolin derivatives with respect to respective subtypes of adenylate cyclases have been performed in various institutes in the past, and already-known values are used for the above experimental values.

When as mentioned above, the first coefficients $D_{V,k}^+$ and the second coefficients $D_{V,k}^-$ are obtained, by substituting them into the activity evaluation expression (6), an activity evaluation expression (8) for the activity $P_V$ of various forskolin derivatives with respect to the type V adenylate cyclase is obtained.

$$P_v = 179.258765 f^+_1 + 120.138157 f^+_2 - 494.709478 f^+_3 - 494.039127 f^+_4 + 255.690223 f^+_5 + 424.37\ 1014 f^+_6 + 107.510211 f^+_7 + 150.958209 f^+_8 + 89.645514 f^+_9 - 81.076721 f^{30}_{10} + 2.163307 f^{30}_{11} - 43.25\ 8603 f^+_{12} - 101.462108 f^+_{13} - 99.8 f^-_1 + 109.597 f^-_2 + 266.931 f^-_3 + 176.945 f^-_4 - 78.839825 f^-_5 - 73.085076 f^-_6 - 78.054163 f^-_7 - 47.5\ 99937 f^-_8 + 79.737810 f^-_9 - 114.660630 f^-_{10} + 32.759411 f^-_{11} + 223.507362 f^-_{12} - 57.729121 f^-_{13} \quad (8)$$

In FIG. 6, the hatched bar charts denote calculated values of the activity $P_V$ of various forskolin derivatives with respect to the type V adenylate cyclase that has been calculated using the activity evaluation expression (8). As shown in FIG. 6, the activity $P_V$ calculated using the activity evaluation expression (8) is found to correlate with the experimental value.

Figure 7:
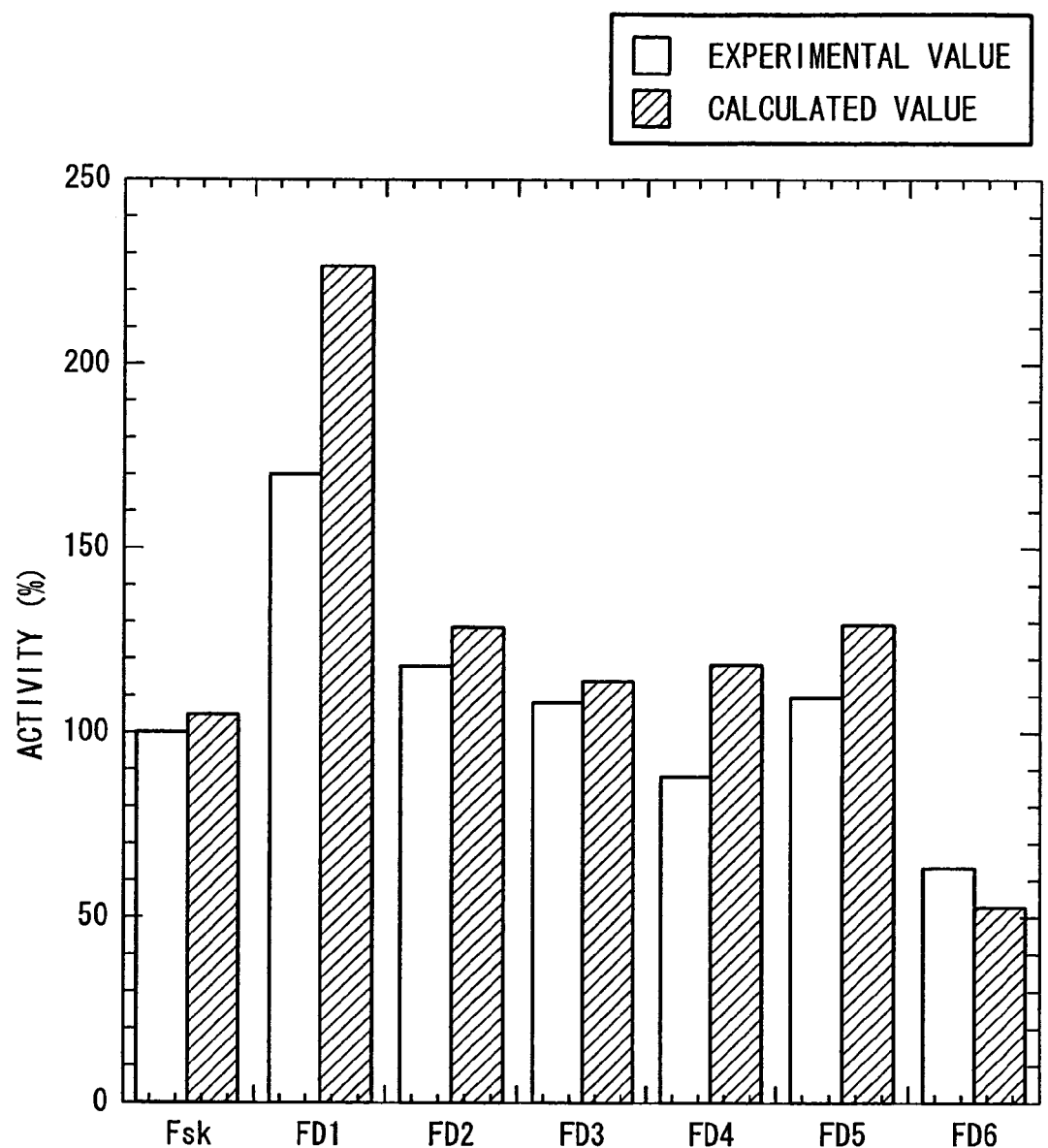
FIG. 7 is a bar chart showing experimental values and calculated values related to activities of various forskolin derivatives with respect to type II adenylate cyclase in one embodiment of the present invention.

Furthermore, FIG. 7 shows activities of the forskolin and the forskolin derivatives "FD1" to "FD6", with respect to subtype i=II, that is, type II adenylate cyclase. The following activity evaluation expression (9) is an activity evaluation expression related to the type II adenylate cyclase derived by obtaining the first coefficient $D_{II,k}^+$ and the second coefficient $D_{II,k}^-$ based on the experimental value of activity shown in FIG. 7, and LUMO$f_k^+$ and HOMO$f_k^-$ shown in FIG. 4 and FIG. 5.

$$P_{II} = 248.938261 f^+_1 - 289.800894 f^+_2 - 539.797479 f^+_3 + 256.934541 f^+_4 - 113.336767 f^+_5 + 55.0117\ 971 f^+_6 + 1.457953453 f^+_7 + 138.843201 f^+_8 + 90.510296 f^+_9 + 82.3516 f^+_{10} + 8.277308 f^+_{11} - 46.229298 f^+_{12} - 26.339115 f^+_{13} - 58.870947 f^-_1 - 22.595841 f^-_2 + 343.956679 f^-_3 - 91.768304 f^-_4 + 93.816112 f_5 - 66.449498 f^-_6 + 69.819391 f^-_7 - 122.564254 f^-_8 - 60.449498 f^-_9 - 56.383834 f^-_{10} - 88.27226341 f^-_{11} + 174.026936 f^-_{12} + 33.533665 f^-_{13} \quad (9)$$

As shown in FIG. 7, the activity $P_{II}$ calculated using the activity evaluation expression (9) is found to correlate with the experimental value. That is, as with the activity evaluation expressions (8) and (9), the activity evaluation expression is previously obtained for each subtype of adenylate cyclase. Then LUMO$f_k^+$ and HOMO$f_k^-$ in the respective analysis points k of the forskolin derivative serving as the evaluation target are calculated by the processing of steps S1 to S13, and they are substituted into the activity evaluation expression that has been prepared for each subtype of adenylate cyclase. As a result, the degree of activity shown by the forskolin derivative selected as the evaluation target, with respect to each subtype of adenylate cyclase, can be obtained by means of calculation.

The present inventors obtained the activity evaluation expression related to adenylate cyclases of other subtypes, obtained the activity for a plurality of forskolin derivatives other than the forskolin derivatives "FD1" to "FD6", based on the activity evaluation expression, evaluated the correlation between this and the experimental values, and confirmed that a high correlation was shown between the experimental values and the calculated values in all cases. That is, the activity evaluation based on the activity evaluation expression (6) can be said to be a highly reliable evaluation method.

Moreover, as the forskolin derivative, theoretically innumerable derivatives can be synthesized. However, as mentioned above, if there are experimental values related to the activity of the forskolin derivatives of a number of types at least twice as many as the number of the analysis points, with respect to a predetermined adenylate cyclase, the activity evaluation expression can be obtained. Therefore, the activity evaluation for other forskolin derivatives can be calculated based on the above activity evaluation expression, enabling evaluation of the activity in a very short time compared to heretofore.

Furthermore, the characteristic of the activity evaluation expression (6) is that a simple calculation of the LUMO$f_k^+$ and HOMO$f_k^-$ for the predetermined analysis points k in the forskolin derivative serving as the evaluation target, by means of numerical calculation, enables calculation of the activity for each subtype of adenylate cyclase. That is, in the process of calculating the activity, the activity can be calculated without any consideration of the molecular structure of the adenylate cyclase serving as the bonding partner of the forskolin derivative. Conventionally, for example in the case where the bonding between a forskolin derivative and adenylate cyclase is evaluated, it is necessary to consider not only the molecular structure of the forskolin derivative, but also the molecular structure of the adenylate cyclase serving as a high molecular compound. Therefore the evaluation has to be performed by a very complicated numerical calculation requiring a long time. However, in the present activity evaluation method, as mentioned above, if, using an already-known activity that has been previously obtained by experiments, the activity evaluation expression (6) is obtained with respect to each subtype of adenylate cyclase, then the activity can be calculated in a short time by performing numerical calculation merely considering the molecular structure of the forskolin derivative.

As described above, according to the present activity evaluation method, the evaluation efficiency of the activity can be remarkably improved. Therefore, by greatly shortening the development term of a drug, superiority with respect to competitors can be ensured, and development costs can be significantly reduced.

The present invention is not limited to the above embodiment, and modified examples such as the followings can be considered.

(1) The above embodiment was described using adenylate cyclase as a high molecular compound, and a forskolin derivative as an evaluation target compound. However, it is not limited to these, and other proteins may be used as a high molecular compound. Moreover the evaluation target compound is not limited to a forskolin derivative.

(2) In the above embodiment, the activity evaluation expression is constituted using LUMO$f_k^+$ showing a nucleophilic reaction, and HOMO$f_k^-$ showing an electrophilic reaction, as Fukui functions. However, it is not limited to these, and the activity evaluation expression may be constituted using a value of a Fukui function showing a radical reaction, that is, a Fukui function showing both of the nucleophilic reaction and the electrophilic reaction.

(3) In the above embodiment, the analysis point k is the C in the benzene rings constituting the forskolin derivative. However, it is not limited to this, and it may be another atom constituting the forskolin derivative.

(4) Although the number of the analysis points k is 13 in the above embodiment, it is not limited to this. However, the number of the analysis points k is preferably large in order to improve the accuracy of the calculated value of activity.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An activity evaluation method for a drug candidate agent comprising:
    setting as k analysis points one or more atoms among atoms constituting a drug candidate agent, wherein the drug candidate agent is a forskolin derivative;
    calculating an activity of said drug candidate agent with respect to a protein, wherein the protein is an adenylate cyclase, based on a predetermined evaluation expression having Fukui function values as variables obtained by numerical calculation for the analysis points; and
    comparing said activity obtained from the calculation with the same activity of said drug candidate agent with respect to said protein obtained from an experiment,
    wherein a first Fukui function value $f_k^+$ showing a nucleophilic reaction and a second Fukui function value $f_k^-$ showing an electrophilic reaction are obtained by means of numerical calculation for each of said k analysis points, and
    wherein an activity P of said drug candidate agent with respect to said protein is calculated based on the following evaluation expression (5) composed of a first coefficient $D_k^+$ related to said first Fukui function value $f_k^+$, and a second coefficient $D_k^-$ related to said second Fukui function value $f_k^-$:

$$P = \sum_{k=1}^{n} (D_k^+ \cdot f_k^+ + D_k^- \cdot f_k^-) \quad (5)$$

(where n is the total number of analysis points k); and
    wherein the results of the calculations are outputted to a user.

2. The activity evaluation method for a drug candidate agent according to claim 1 further comprising: applying a least-squares method to an activity experimental value $P_e$ related to a plurality of derivatives of said drug candidate agent, and a first Fukui function value $f_k^+$ and a second Fukui function value $f_k^{31}$ related to each of said derivatives, to thereby calculate a first coefficient $D_k^+$ showing a relation between the activity P and said first Fukui function value $f_k^+$, and a second coefficient $D_k^-$ showing a relation between the activity P and said second Fukui function value $f_k^-$.

3. The activity evaluation method for a drug candidate agent according to claim 1 further comprising: solving as simultaneous equations a plurality of equations obtained by substituting an activity experimental value $P_e$ related to a plurality of derivatives of said drug candidate agent, and a first Fukui function value $f_k^+$ and a second Fukui function value $f_k^-$ related to said derivatives, into said evaluation expression, to thereby calculate said first coefficient $D_k^-$ and said second coefficient $D_k^-$.

4. The activity evaluation method for a drug candidate agent according to claim 2 further comprising setting as an analysis point, among atoms constituting each of said derivatives of said drug candidate agent, an atom which is commonly present in each of said derivatives.

5. The activity evaluation method for a drug candidate agent according to claim 3 further comprising setting as an analysis point, among atoms constituting each of said derivatives of said drug candidate agent, an atom which is commonly present in each of said derivatives.

* * * * *

UNITED STATES PATENT AND TRADEMARK OFFICE
CERTIFICATE OF CORRECTION

PATENT NO. : 7,337,073 B2
APPLICATION NO. : 11/442478
DATED : February 26, 2008
INVENTOR(S) : Eguchi et al.

It is certified that error appears in the above-identified patent and that said Letters Patent is hereby corrected as shown below:

Item (75) Inventors should read:
 Haruki Eguchi, Yokohama-shi (JP);
 Yoshihiro Ishikawa, 1-19-8, Shinjuku, Shinjuku-ku, Tokyo (JP);
 Kousaku Iwatsubo, Yokohama-shi (JP)

Signed and Sealed this

First Day of July, 2008

JON W. DUDAS
*Director of the United States Patent and Trademark Office*